United States Patent [19]
Bao et al.

[11] Patent Number: 5,587,130
[45] Date of Patent: Dec. 24, 1996

[54] SELECTED AREA ADHESION AND SURFACE PASSIVATION OF METAL FILMS

[75] Inventors: Qingcheng Bao, Tempe; Ian Sorensen, Phoenix; William Glaunsinger, Chandler, all of Ariz.

[73] Assignee: Arizona Board of Regents, Tempe, Ariz.

[21] Appl. No.: 353,448

[22] Filed: Dec. 9, 1994

Related U.S. Application Data

[63] Continuation-in-part of Ser. No. 31,610, Mar. 15, 1993, Pat. No. 5,466,605.

[51] Int. Cl.$^6$ .................................................. G01N 27/12
[52] U.S. Cl. ........................... 422/88; 422/90; 427/383.1; 338/34
[58] Field of Search ................................ 422/88, 90, 98; 427/123, 125, 258, 259, 305, 306, 383.1; 228/122.1, 193, 194; 338/34

[56] References Cited

U.S. PATENT DOCUMENTS

| | | | |
|---|---|---|---|
| 3,714,562 | 1/1973 | McNerney | 324/65 R |
| 4,322,457 | 3/1982 | Baron et al. | 427/259 |
| 4,551,629 | 11/1985 | Carson et al. | 250/578 |
| 4,724,008 | 2/1988 | Bell et al. | 134/2 |
| 4,952,904 | 8/1990 | Johnson et al. | 338/36 |
| 5,134,080 | 7/1992 | Bell et al. | 436/123 |
| 5,367,283 | 11/1994 | Lauf et al. | 338/34 |

OTHER PUBLICATIONS

M. A. George, et al.; *Cr Diffusion through Au Films*; pp. 59–72.

G. Majni, et al.; *Interdiffusion of Cr and AU Films on Si*; pp. 15–19.

R. E. Hampy, et al.; *Interfacial behavior of Cr–Au films*; pp. 25–30.

P. H. Holloway, et al.; Journal of Applied Physics, vol. 47, No. 9, Sep. 1976: *Analysis of grain–bounder diffusion in thin films: Chromium in gold*; pp. 3769–3775.

S. K. Kurinec, et al.; *Heat Treatment of Au/Ni Composites*; pp. 247–255.

*Primary Examiner*—Jeffrey Snay
*Attorney, Agent, or Firm*—Meschkow & Gresham, P.L.C.

[57] ABSTRACT

A thin film device having a selectively passivated surface is provided. An embodiment of the device is particularly suited to detection of chemical constituents by selective adsorption, where the selectively passivated surface is inert to the chemical constituent being detected. A method of fabrication of the device is also provided in which the selective passivation is achieved by selectively applying the metallic adhesive to the substrate. The migration of the metallic adhesive through the thin film layer is essentially normal to the surface of the substrate, thereby limiting the passivation of the thin film layer to the surface areas directly overlying the metallic adhesive.

28 Claims, 3 Drawing Sheets

SELECTED AREA ADHESION AND SURFACE PASSIVATION OF METAL FILMS

CROSS-REFERENCE TO RELATED APPLICATION

This application is a continuation-in-part of application Ser. No. 08/031,610 filed Mar. 15, 1993, now U.S. Pat. No. 5,466,605.

BACKGROUND OF THE INVENTION

This application relates to bonding of metal films to semiconductor and other substrates, particularly to bonding of metal films to substrates using metallic adhesives, and more particularly to bonding while controlling the surface passivation caused by such metallic adhesives.

Conductive metals are commonly used in integrated circuits and other semiconductor devices to form a variety of structures including the conductive interconnects between semiconductor elements, and the wire bond pads used to connect the device to the chip carrier. Many of these conductive metals, however, have poor adhesion to the substrates commonly used in the industry. Accordingly, bonding of metal films to semiconductor substrates is a widely popular technique in the manufacture of integrated circuits. More recently, bonding of metal films to polyimide and other polymer substrates has become a popular technique used in the manufacture of flexible printed circuit boards and other devices.

A variety of techniques are commonly employed to bond the films to the substrates. Common techniques include surface roughening, irradiation, sputtering, use of chemical modifiers, and use of interfacial metallic adhesives. Of these, use of interfacial metallic adhesives is probably the most popular and the most practical method. Metals employed as metallic adhesives are oxygen-active metals that also have a solid solubility in the conductive metal film to be adhered. Such metallic adhesive materials include chromium, titanium, and aluminum. Use of these oxygen-active metallic adhesives, however, has led to the problem of degradation of the conductive film surface due to grain-boundary diffusion of the metallic adhesive to the surface of the conductive film.

Ordinarily, to maximize the area for bonding, the metallic adhesive is applied to the substrate in a pattern that substantially matches the pattern of the metal film to be attached and the conductive metal film is applied over the metallic adhesive. When the device is exposed to oxygen, the metallic adhesive migrates through the metal film and forms oxides on the surface, which passivates substantially all of the surface of the metal film. The passivation process is accelerated by temperature. Usually, electronic devices rely on the bulk conductive properties of the metal films applied to the substrate, so the surface condition of the metal film after the device is fabricated is of little consequence and a passivated surface may even be desirable. For many applications, however, it is important to avoid passivation of the surface of the metal film. Control of surface passivation is particularly important for metal-film chemical sensors, which rely on a surface reaction of the metal film to produce a response.

Examples of such chemical sensors include the apparatus disclosed in U.S. Pat. No. 3,714,562 to McNerney (the '562 patent) in which a chemical sensor composed of a gold film on an insulating substrate selectively adsorbs mercury to cause a gradual change in the resistance of the gold film. The chemical switch disclosed in the aforementioned co-pending application Ser. No. 08/031,610, now U.S. Pat. No. 5,466,605, incorporated herein by reference, comprises a noble metal film on an insulating substrate that selectively adsorbs chlorine or other reactive components to cause an abrupt change in the resistance of the film. In these and similar devices, it is desirable to achieve satisfactory adhesion of the device to the substrate with minimal passivation of the active surface of the metal film. Otherwise, the surface passivation will eventually render the device incapable of adsorbing the target chemical.

Heretofore, metal-film chemical sensors have used ordinary metal film adhesive techniques to attach the sensor elements to their substrates and, as a consequence, have had a limited service life. A gold film sensor of the type disclosed in the '562 patent used to detect mercury must be heated after a sample is taken to desorb the adsorbed mercury species and thereby regenerate the sensor for another cycle of operation. Each time the sensor is heated, however, the passivation of the sensor is exacerbated. Frequently, such sensors are rendered unusable after fewer than a few hundred cycles. What is needed then, is a method of attaching metal films to substrates that provides adequate adhesion for structural integrity, yet eliminates the adverse surface passivation effects of the metallic adhesives.

Accordingly, it is a principal object of this invention to provide a method for attaching metal films to substrates with metallic adhesives that provides adequate adhesion while eliminating the adverse surface passivation effects of the metallic adhesive. A further object of this invention is to provide a chemical sensor having an active element and a reference element fabricated by the same process steps as the active element, but having a purposefully passivated surface.

SUMMARY OF THE INVENTION

The present invention takes advantage of the fact that where a relatively thin metal film is attached to a substrate by means of an interfacial metallic adhesive, the migration of the metallic adhesive through the metal film is in a direction substantially normal to the surface of the film. Thus, the surface passivation of the metal film may be controlled by limiting the adhesive to selected areas underneath the film.

In the preferred embodiment of the present invention a pattern of metallic adhesive is formed on a substrate by applying the adhesive to selected areas of the substrate. The metal film is then applied to the substrate over the adhesive so that it covers substantially all of the adhesive and also some portion of the substrate directly. The assembly comprising the substrate, adhesive, and the metal film is then exposed to an atmosphere containing a reactive agent such as oxygen. As it reacts with the atmospheric agent, the metallic adhesive forms a stable passivation layer on the surface of the metal film. Because the migration of the metallic adhesive is substantially normal to the surface of the substrate, the passivation layer on the film is substantially identical to the pattern of the underlying adhesive.

A further aspect of the invention provides for a chemical sensor in which the adhesive layer is applied in a regular pattern only underneath the regions of the metal film where the electrical connections are to be made. These electrical connection regions may be wire bond pads, pressure contact areas, or other regions where external loads associated with electrical connections are likely to be applied. This method provides a stable platform for making electrical contact and for securing the unpassivated structure.

A further aspect of the invention provides for a chemical sensor pair or array in which matched sensors and reference elements are fabricated by the same process steps, but with interfacial metallic adhesive underneath the reference elements in their entirety. By fabricating the sensors and reference elements simultaneously, the matching of electrical properties is simplified. However, by incorporating interfacial metallic adhesive underneath the reference elements, the surfaces of the reference elements are passivated and rendered inert to the chemical species the sensor elements are designed to detect. These matched sensors and reference elements are ideally suited for use in a bridge circuit used to amplify the response of the sensor element.

BRIEF DESCRIPTION OF THE DRAWINGS

The above and other objects, aspects, features and attendant advantages of the present invention will become apparent from a consideration of the ensuing detailed description of presently preferred embodiments and methods thereof, taken in conjunction with the accompanying drawings, in which.

DESCRIPTION OF THE PREFERRED EMBODIMENTS AND METHODS

Figure 1A:
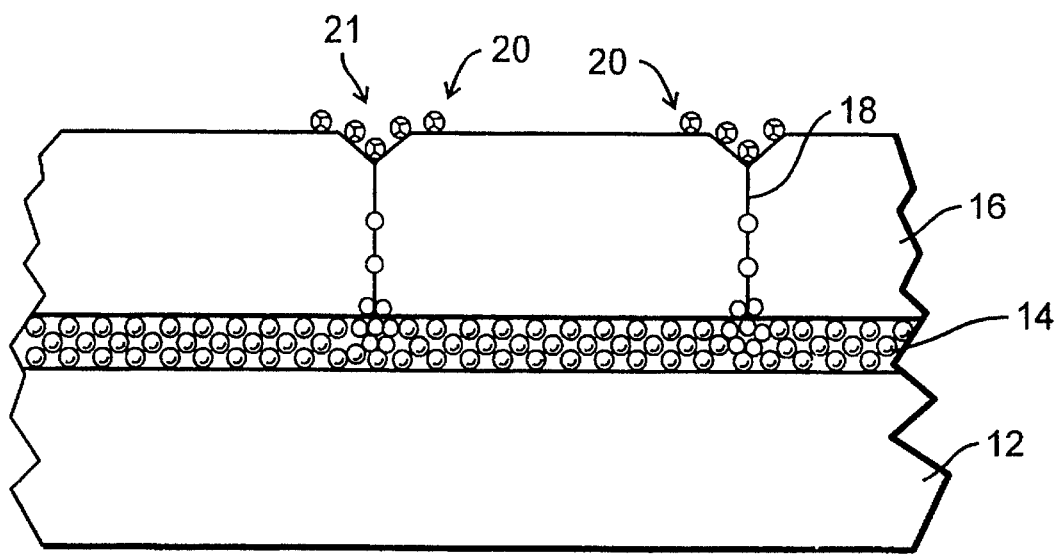
FIG. 1(a) is a cross section illustrating metallic adhesive bonding of a thin metal film to a substrate and passivation of the thin metal film surface by grain-boundary migration of relatively thin deposits of a reactive metallic adhesive material.

FIG. 1 is a cross sectional view of a segment of a device comprising a metal film bonded to a substrate. Metal film 16 is attached to substrate 12 by means of metallic adhesive 14. Metallic adhesive 14 will typically be chosen from a group of metals having affinity for the substrate and having solid solubility in the metal film to be attached. Accordingly, some of the metallic adhesive 14 will form bonds with the substrate and some with the metal film. The remainder of metallic adhesive 14 will remain unbonded. Metal film 16 will inherently contain numerous grain boundaries 18 that provide a path for the unbonded metallic adhesive 14 to migrate to the surface. If the device is exposed to an atmosphere containing oxygen (or other constituents having sufficient bond energy to form a metallic adhesive compound having a lower energy state than the pure metallic adhesive) strong thermodynamic forces cause the unbonded metallic adhesive to migrate through the metal film to form stable surface compounds 20.

For example, where metal film 16 is gold and substrate 12 is polyimide, metallic adhesive 14 is typically chromium. Upon exposure of the device to the atmosphere, the chromium will eventually migrate to the surface of the gold to form chromium oxide ($Cr_2O_3$). This grain-boundary migration can be accelerated by heating the substrate-metal film structure.

It can be recognized from FIG. 1(a) that for a relatively thin (<50 Å) deposit of metallic adhesive, little unbonded metallic adhesive 14 remains. Accordingly, the migrating adhesive forms clusters of stable compounds 20 that decorate the grain boundaries and the immediately adjacent metal film surface. The process results in partial passivation of the metal film surface.

Figure 1B:
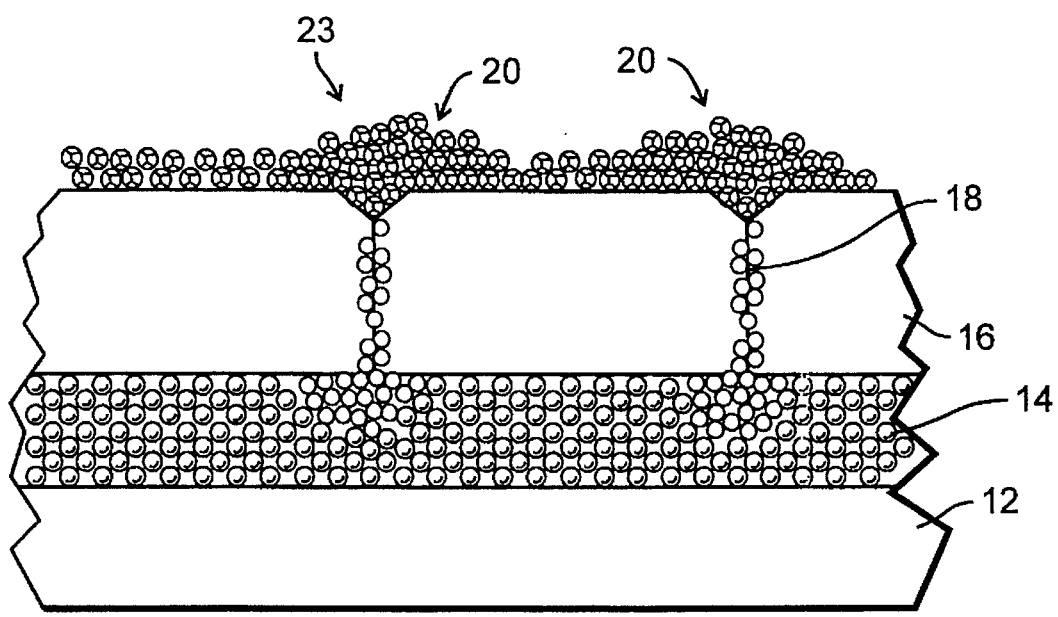
FIG. 1(b) is a cross section illustrating metallic adhesive bonding of a thin metal film to a substrate and passivation of the thin metal film surface by grain-boundary migration of relatively thick deposits of a reactive metallic adhesive material.

Referring to FIG 1(b), relatively thicker (>200 Å) deposits of metallic adhesive leave sufficient unbonded adhesive 14 to migrate through the grain boundaries in quantity. Accordingly the migrating adhesive forms laterally overlapping surface "blooms" of stable compounds 20 that can completely passivate the metal film surface. The stable compound deposits, in conjunction with the metallic adhesive in the grain boundaries and at the metal film-substrate interface, also form "rivet-like" structures that enhance adhesion.

Although the detailed configuration of the grain boundaries will depend upon numerous factors, including the microstructure of the substrate and the film deposition conditions, the grain boundaries will always provide the fastest diffusive path for the metallic adhesive to the metal film surface. For a metal film 16 whose thickness is much less than its planar dimensions, such grain-boundary diffusion causes the migrating metallic adhesive 14 to move in a direction substantially normal to the surface of the substrate 12, in essence translating an image of the metallic adhesive 14 through the metal film 16 to its surface. Therefore, any passivation of the metal film surface is confined substantially to the area defined by the underlying interfacial metallic adhesive. This phenomenon can be used to achieve a desired degree of adhesion enhancement while controlling metal film surface passivation by placing the metallic adhesive in only selected areas, such as where adhesion is to be enhanced or where electrical contact to the metal film is to be made.

Figure 2:
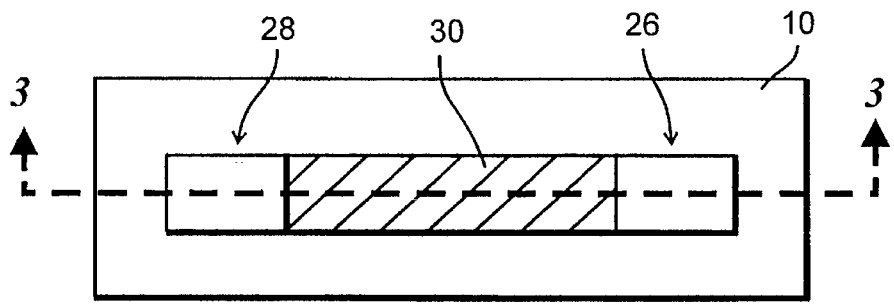
FIG. 2 is a perspective top view of a device comprising a thin metal film on a substrate with reactive metallic adhesive deposited only on selected areas of the substrate where electrical contact is to be made.
Figure 3:
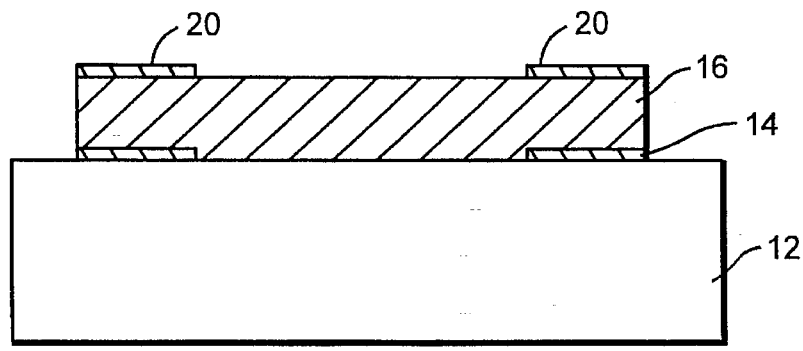
FIG. 3 is a cross sectional view of the device of FIG. 2 taken along line 3—3.

FIG. 2 is a top view of an embodiment of the present invention in which thin metal film 16 comprises a gold film of from a minimum of about 20 Å to a maximum of about 2,000 Å, but preferably about 500 Å thick attached to substrate 12 with a thin layer of a metallic adhesive material 14. The layer of metallic adhesive comprises a layer of chromium of about 20 Å to a maximum of about 1,000 Å but preferably about 200 Å thick. In the embodiment of FIG. 2, however, adhesive material 14 is deposited only in the contact pad areas 26 and 28. FIG. 3 is a cross sectional view of the sensor of FIG. 2 taken along line 3—3. As may be noted, the embodiments depicted in the figures share similar elements, accordingly, similar elements are identified with like numbers. The device of FIGS. 2 and 3 may be fabricated by using masks to direct the deposition of the metallic adhesive 14 onto only the electrical contact pad areas 26 and 28 for relatively large-area deposits (>10 microns) and by standard lithographic methods for smaller-area deposits (>0.2 microns), followed by deposition of the thin metal film 16 over the adhesive contact pads and directly onto the substrate 12 in the sensor region 30.

The chromium adhesive and the gold film can be deposited sequentially in an evaporation system operating at less than $10^{-6}$ Torr to minimize any oxidation of the chromium prior to application of the gold film. The device is then annealed at a temperature of 350° C. for 10 minutes to substantially advance the passivation process. Using this procedure, chromium metallic adhesive as thin as 20 Å underlying a 1,000 Å thick gold layer on a polyimide substrate results in improved adhesive bonding and partial passivation of the sensor surface. Deposits of about 200 Å or more in the same configuration always result in total passivation of the contact pad surface. Such passivation will render the electrical contact pads completely inert, so that they do not participate in surface chemical reactions, such as those occurring in the sensor region 30 of the device.

The device of FIGS. 2 and 3 also provides for highly durable electrical contacts pads capable of withstanding connections made by bringing the contact pads into abrasive contact with conventional electrical edge connectors, which abrade the passivated contact area to make electrical contact with the thin metal film. In this configuration, the adhesive material effectively anchors the two ends of the thin metal film to the substrate to increase its effective adhesion and physical stability. Such anchoring will become more effective as the distance between the electrical contact pads is diminished.

Several key features of this invention have been demonstrated for a thin metal film chemical sensor that operates by either adsorbing or reacting with one or more chemical components that impinge on its surface. The test structure was essentially that shown in FIGS. 2 and 3, where (i) the substrate 12 comprised a silicon wafer with a passivation layer of either silicon dioxide or silicon nitride produced by standard procedures to minimize electrical contact between the sensor and the substrate; (ii) the metallic adhesive 14 comprised a thin layer of chromium deposited by vacuum evaporation only over the areas where electrical contact to the chemical sensor was to be made; and (iii) a chemical sensor sensitive to mercury vapor consisting of thin metal film 16 comprising a gold film deposited by vacuum evaporation over both the electrical contact pads 26 and 28 and the desired chemically active sensor area 30. This test structure was preferred because of the very weak adhesion of the gold film to a passivated silicon substrate. The areal dimensions of the electrical contact pads were about 600 microns×700 microns and the metal film was about 22,500 microns×120 microns.

In the first test, a 1,000 Å layer of pure gold was deposited in the pattern depicted in FIG. 2 without any underlying chromium adhesive. The test structure was then removed from the evaporator and annealed in air at 350° C. for 10 minutes. A standard cellophane-tape adhesion test revealed that the gold film was completely removed after the first test. In fact, the gold-film adhesion was so weak that even a modest stream of pressurized air was able to disrupt the film.

In the second test, a 200 Å layer of chromium was first deposited over the contact pad areas 26 and 28, followed by the deposition of 1,000 Å of gold comprising the thin metal film 16 shown in FIG. 2. The same annealing conditions were used as in the first test to substantially advance the chromium migration process shown in FIG. 1(b). Application of the cellophane-tape test revealed that only the contact pads remained after the first test. These contact pads also remained intact even after multiple applications of the cellophane-tape test. Both the surfaces of the contact pads 26 and 28 and the thin metal film 16 were analyzed by x-ray photoelectron spectroscopy to define the distribution of chromium and gold on the surface of the metal film structure in FIG. 2. Only chromium, in the form of $Cr_2O_3$, was found in the electrical contact pad areas, whereas relatively pure gold was found in the sensor region of the device. An additional device constructed using the same techniques revealed that the device exhibited an extremely high sensitivity for mercury vapor (<1 µg/m$^3$), which was attributed to the absence of chromium passivation of the sensor region. The same device also exhibited very little drift from its nominal value, which was attributed to the fact that the electrical contact areas were completely passivated and, therefore, did not exhibit any response to the mercury.

In a third test, a device was constructed with an ultra-thin layer (approximately 20 Å) of chromium underlying the entire sensor in an attempt to limit the surface passivation by controlling the amount of chromium available to migrate to the surface. Even with the ultra-thin metallic adhesive layer, however, the sensitivity of the device to mercury was substantially poorer than the device with 200 Å of metallic adhesive under the electrical pads alone. This further confirms that the chromium migration is substantially normal to the surface and that the passivation remains confined to the surface of the contact pads 26 and 28 as shown in FIG. 2.

Figure 4:
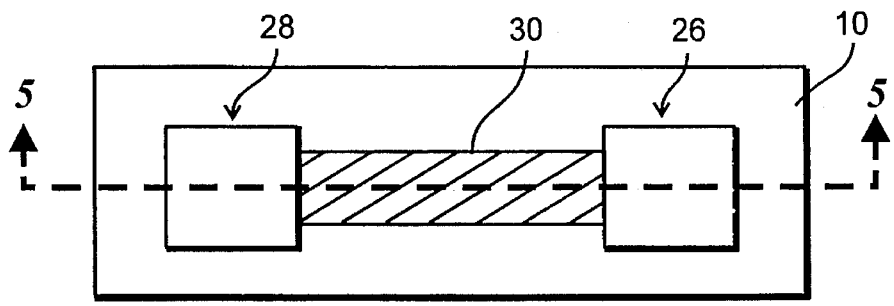
FIG. 4 is a top view of a device comprising similar to the device of FIG. 2 including metallization suitable for wire bonding to the electrical contact pads of a thin metal film.
Figure 5:
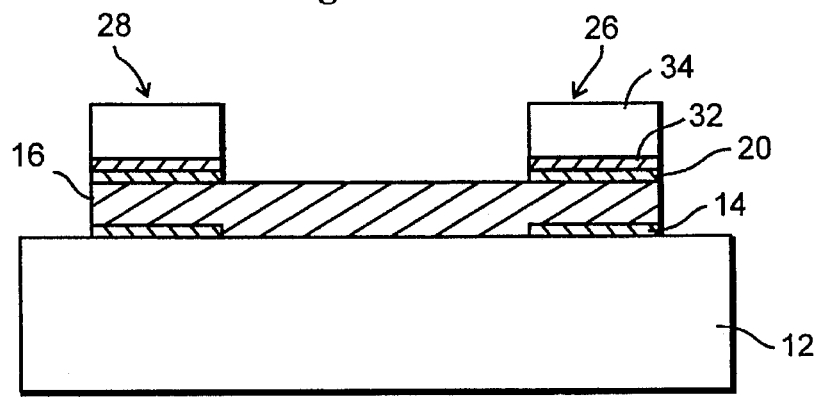
FIG. 5 is a cross sectional view of the device of FIG. 4 taken along line 5—5.

Especially suited to smaller devices, permanent, rather than temporary, electrical contact to the thin metal film can be made by conventional wire bonding, as illustrated by the structure in FIG. 4. FIG. 5 is a cross sectional view of the device of FIG. 4 taken along line 5—5. This structure can be fabricated by first depositing a metallic adhesive layer 14 on the substrate only on the area defined by the electrical contact pads 26 and 28 by using a contact-pad mask. A very thin (<200 Å) continuous overlayer of metal film 16 is immediately deposited on top of the reactive adhesive layer to serve as a protective coating to prevent excessive formation of stable metallic adhesive compounds. A mask for depositing the thin metal film 16 is then installed in the evaporator and the metal film is deposited. The contact-pad mask is then re-installed on the evaporator and a second layer of metallic adhesive 32 is deposited directly over the metal film in the same area as the metallic adhesive 14. Then, a relatively thick layer of a common metal used in wire bonding, such as aluminum 34, is deposited directly over the top layer of metallic adhesive 32. Test electrical-contact-pad structures of the type shown in FIGS. 4 and 5 were fabricated in a conventional evaporation system operating at $10^{-6}$ Torr. Reliable wire bonds to the electrical contact pads on ceramic alumina, passivated silicon substrates, and even polyimide were made by using 25-micron diameter aluminum wire and a combination of heat and ultrasonic vibration, which resulted in a bonding area of approximately 25–50 microns. Gold can be used instead of aluminum for both the electrical contact pads in FIGS. 4 and 5 as well as for the wire bonding process, but this configuration is less cost effective and robust than the one employing aluminum.

Figure 6:
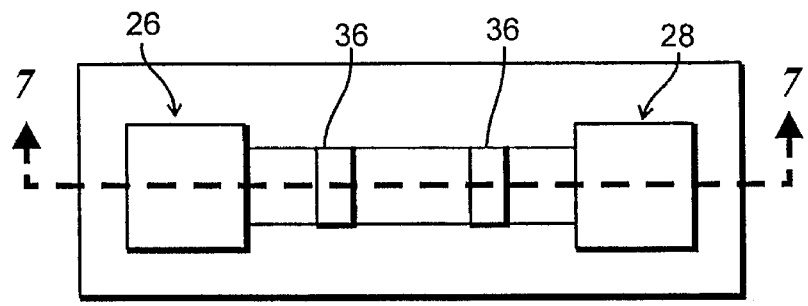
FIG. 6 is a perspective top view of a thin metal film on a substrate with a reactive metallic adhesive layer deposited in selected areas where electrical contact is made as well as in selected areas where the remainder of the metal film is deposited.
Figure 7:
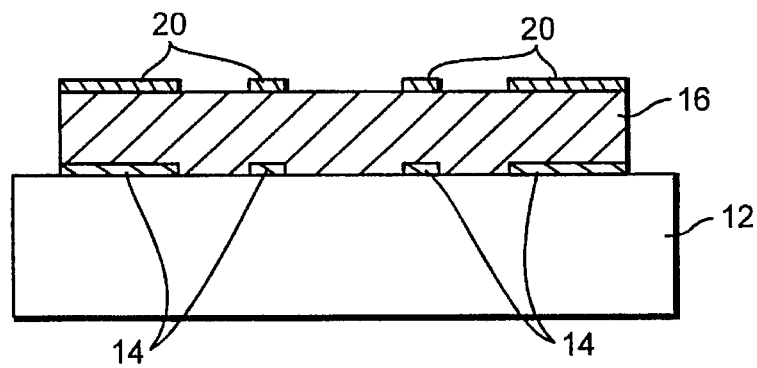
FIG. 7 is a cross sectional view of the device of FIG. 6 taken along line 7—7.

The concept of selected-area adhesion and passivation can also be utilized to obtain a desired degree of adhesion and physical stability of a thin metal film as well as to fabricate thin-metal-film chemical sensor devices. FIG. 6 shows a perspective top view of a metal film 16 on a substrate 12 with a metallic adhesive layer 14 deposited in contact pad areas 26 and 28 as well as in selected areas 36 where the remainder of the metal film is deposited. FIG. 7 is a cross sectional view of the device of FIG. 6 taken along line 7—7. This design not only results in durable electrical contact pads 26 and 28, but also allows additional improved adhesion of the metal film by creating selected anchoring areas 36 between the film and substrate. These anchoring areas locally "rivet" the metal film to the substrate. The pattern of these anchoring areas may be either engineered or random. The former arrangement may be produced by using specially designed masks to direct the deposition of the adhesive metal onto only selected areas of the substrate for relatively large-area deposits (>10 microns) and by standard lithographic methods for very small-area deposits (>0.2 microns). The random pattern may be produced by making an ultrathin (less than several atomic layers in thickness) deposit of metallic adhesive on the substrate, in which case the adhesive metal will typically aggregate to form randomly distributed islands of different sizes in different regions of the substrate prior to deposition of the metal film. Key advantages of both approaches are that (i) rupture of the film due to extended physical defects, such as cracks, can be prevented and (ii) if excess metallic adhesive is deposited only in selected areas, then grain-boundary diffusion limits the passivation of the metal surface by the adhesive to approximately the area of the metallic adhesive deposit.

Figure 8A:
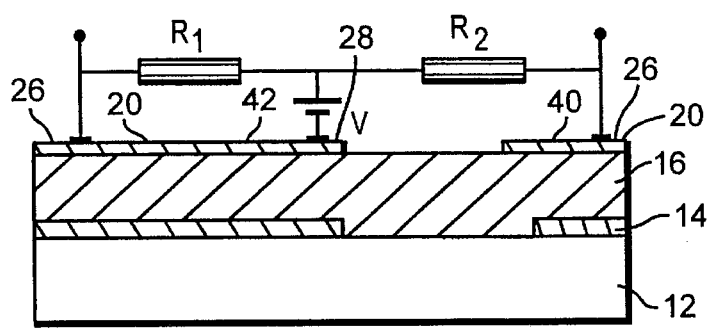
FIG. 8(a) is a cross sectional view of a matched sensor-reference element pair.
Figure 8B:
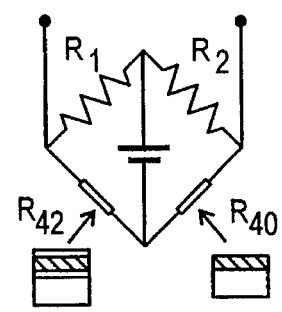
FIG. 8(b) is a schematic representation of a bridge circuit incorporating the matched sensor-reference element pair of FIG. 8(a).

FIG. 8(a) is a cross sectional view of a matched sensor-reference element pair, illustrating how the concept of selected-area adhesion and passivation can be used to create an integrated thin-film chemical sensor device consisting of an active chemical sensor and an inert reference element. The chemical sensor device 40 consists of an active surface whose purpose is to selectively react with specific chemical components. The sensor device 40 includes passivated contact-pad areas 26 and 28 where either temporary or permanent electrical connections can be made, as discussed with reference to FIGS. 2–5. The reference element 42 is very similar to the chemical sensor in electrical resistance, including properties such as thermal drift, except that its surface is completely passivated with stable compounds 20 so that it will not respond to any chemical components. The reference element 42 can be fabricated by applying the metallic adhesive layer 14 uniformly on the electrical-contact-pad area as well as on the region between the electrical contact pads where the reference element is deposited. Wire bonding to the sensor is facilitated by having both the sensor and the reference elements adjacent to each other on the same side of the substrate. Referring also to FIG. 8(b), electrical contacts to the sensor may be made such that the chemical sensor and reference elements form two arms of a conventional electrical bridge containing, for example, balancing resistors $R_1$ and $R_2$. The balancing resistors are adjusted so that no current flows in the arm separating the chemical sensor (shown as $R_{40}$) and reference element (shown as $R_{42}$) before the chemical component(s) to be detected or analyzed are passed over the sensor and reference surfaces, so that a "null" condition is created. Subsequent exposure of the sensor 40 and reference element 42 to the sample and selective reaction of the sample with the surface of the chemical sensor will unbalance the bridge, the degree of which can be amplified and measured by conventional means.

Figure 8C:
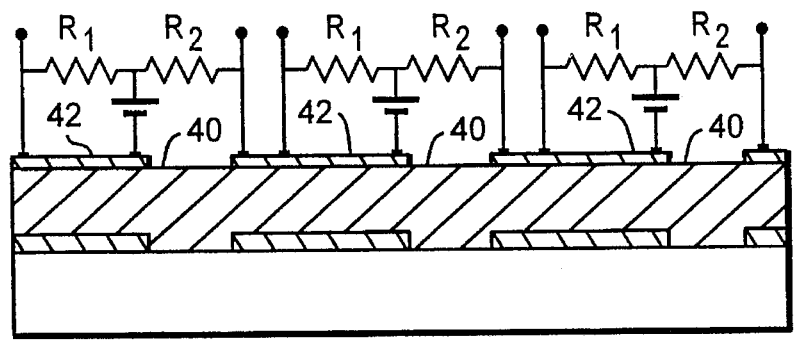
FIG. 8(c) is a cross sectional views of an array of matched sensor-reference element pairs.

The integrated design shown in FIG. 8(a) can be extended to an array of several identical devices fabricated on a single thin metal film, as shown in FIG. 8(c). Use of an array increases the redundancy of the overall system, so that failure of a particular device does not interrupt the detection process. Such an array also improves the precision of the measurement by the square root of the number of active devices, according to standard theory of signal averaging. The design in FIG. 8(c) can also be extended to incorporate sensor-reference pairs having different metal-film compositions for the selective detection of multiple chemical components, without sacrificing redundancy or concomitant signal enhancement.

Although certain preferred embodiments and methods have been disclosed herein, it will be apparent from the foregoing disclosure to those skilled in the art that variations and modifications of such embodiments and methods may be made without departing from the true spirit and scope of the invention. Accordingly, it is intended that the invention shall be limited only to the extent required by the appended claims and the rules and principles of applicable law.

What is claimed is:

1. A method of affixing metal film to a substrate with controlled passivation of said metal film, comprising:

applying a thin layer of a metallic adhesive to a portion of a surface of the substrate to form an adhesive pattern;

applying the metal film to the surface of the substrate over the metallic adhesive so that said metal film is in contact with at least some portion of said metallic adhesive and at least some portion of the surface of the substrate;

exposing an assembly including the substrate, the metallic adhesive, and the metal film to an atmosphere containing a constituent having sufficient bond energy to form a compound having a lower energy state than the pure metallic adhesive, to cause the metallic adhesive to migrate to an exposed surface of said metal film and form a stable compound, thereby passivating a portion of the exposed surface of said metal film corresponding to said adhesive pattern.

2. The method of claim 1 wherein the exposing of said assembly is to an atmosphere containing oxygen.

3. The method of claim 1 wherein the metallic adhesive forms structures through the metal film to pin the metal film to the substrate.

4. The method of claim 1 wherein the metallic adhesive migrates substantially normal to the exposed surface of the substrate.

5. The method of claim 4 wherein the metallic adhesive is applied in an ultra-thin layer to form a random pattern.

6. The method of claim 4 wherein the metallic adhesive is applied in a predetermined regular pattern.

7. The method of claim 6 wherein the metallic adhesive is applied only in regions suitable for making electrical contact.

8. The method of claim 6 wherein the metallic adhesive is applied in specific areas to maximize adhesion.

9. A thin film device formed by:

selectively applying a thin layer of a metallic adhesive to a surface of a substrate to form an adhesive pattern;

applying a metal film to the surface of the substrate over the metallic adhesive so that said metal film is in contact with at least some portion of said metallic adhesive and at least some portion of the surface of the substrate;

exposing an assembly including the substrate, the metallic adhesive, and the metal film to an atmosphere containing a constituent having sufficient bond energy to form a metallic adhesive compound having a lower energy state than the pure metallic adhesive to cause the metallic adhesive to migrate to an exposed surface of said metal film and form a stable compound, thereby passivating a portion of the exposed surface of said metal film corresponding to said adhesive pattern.

10. The device of claim 9 wherein the atmospheric constituent is oxygen.

11. The device of claim 9 wherein the metallic adhesive forms structures through the metal film to pin the metal film to the substrate.

12. The device of claim 9 wherein the metallic adhesive is applied in a predetermined regular pattern.

13. The device of claim 9 wherein the metallic adhesive is applied only in regions suitable for making electrical contact.

14. The device of claim 9 wherein the metallic adhesive is applied in specific areas to maximize adhesion.

15. The device of claim 9 wherein the metallic adhesive is applied in an ultra-thin layer to form a random pattern.

16. A thin film device comprising:

a substrate having a surface;

a film of metallic adhesive affixed to the surface of said substrate covering less than the total area of said surface to form an adhesive pattern;

a metal film applied to the surface of said substrate overlapping directly said metallic adhesive and overlapping directly at least some portion of the surface of said substrate; and a passivation layer overlapping directly said metal film, said passivation layer comprising stable compounds of the metallic adhesive substantially confined to a region corresponding to the underlying adhesive pattern, wherein said passivation layer is formed by migration of said metallic adhesive through said metal film.

17. The device of claim 16 wherein the stable compounds of metallic adhesive are scattered throughout the region overlapping the adhesive pattern to form isolated fastening structures through the metal film to the underlying metallic adhesive.

18. The device of claim 16 wherein said metallic adhesive has a thickness of from 20 to 1000Ångstroms.

19. The device of claim 16 wherein the metal film has a thickness of from 20 to 2000Ångstroms.

20. The device of claim 16 wherein the metallic adhesive has thickness of from 5% to 20% of the thickness of the metal film.

21. The device of claim 16 wherein said passivation layer comprises a contiguous layer covering substantially all of the region directly overlapping the adhesive pattern.

22. The device of claim 21 wherein the adhesive is affixed to the substrate in a region underlying an electrical contact pad to fasten said electrical contact pad to the substrate and to passivate the surface of said electrical contact pad.

23. The device of claim 22 further including a device structure, said device structure comprising metal film overlapping the substrate directly, said device structures having a substantially unpassivated exposed surface.

24. The device of claim 23 wherein the device structure comprises a sensor element to detect a target gas in a gaseous mixture.

25. The device of claim 24 further including a reference element, said reference element comprising a structure electrically similar to said device structure overlapping said metallic adhesive and having a passivation layer covering substantially all of the exposed surface of said reference element.

26. The device of claim 25 further including:

a plurality of sensor and reference elements, said plural sensor and reference elements being of substantially identical construction to said sensor and reference element.

27. The device of claim 25 further including:

a second sensor and a second reference element, said second sensor and reference element being dissimilar to said sensor and reference element.

28. A chemical sensor comprising:

a substrate having a surface;

a film of metallic adhesive affixed to the surface of said substrate covering less than the total area of said surface; and a metal film having an exposed surface, said metal film affixed to the surface of said substrate overlapping substantially all of said metallic adhesive and overlapping at least some portion of the surface of said substrate directly;

a passivation layer comprising stable compounds of the metallic adhesive on the exposed surface of said metal film, said passivation layer substantially confined to a region directly over the adhesive pattern, wherein said passivation layer is formed by migration of said metallic adhesive through said metal film;

whereby the exposed surface of said metal film overlapping the substrate directly is unpassivated and capable of reacting with selected chemical species and the exposed surface of said metal film in the region overlapping the metallic adhesive is passivated and incapable of substantial reaction with the selected chemical species.

* * * * *